United States Patent [19]

Gisser et al.

[11] Patent Number: 5,387,728

[45] Date of Patent: Feb. 7, 1995

[54] PROCESS FOR THE PREPARATION OF HEXAFLUOROPROPENE DIMERS HAVING A HIGH PROPORTION OF PERFLUORO-(4-METHYL-2-PENTENE)

[75] Inventors: Alfons Gisser, Burgkirchen; Konrad von Werner, Garching, both of Germany

[73] Assignee: Hoechst Aktiengesellschaft, Frankfurt, Germany

[21] Appl. No.: 111,643

[22] Filed: Aug. 25, 1993

[30] Foreign Application Priority Data

Aug. 27, 1992 [DE] Germany .................. 4228592

[51] Int. Cl.$^6$ .................................. C07C 17/02
[52] U.S. Cl. .................................. 570/153
[58] Field of Search ............................ 570/153

[56] References Cited

U.S. PATENT DOCUMENTS 2,918,501 12/1959 Brehm et al. .
3,917,724 4/1975 Martini .
4,042,638 8/1977 Ozawa et al. .

FOREIGN PATENT DOCUMENTS 3081233 4/1991 Japan ..................... 570/153
910371 11/1962 United Kingdom ........ 570/153

OTHER PUBLICATIONS

Dresdner, R. D., et al, *J. Org. Chem.* 30:3524–3526 (1965).
Halasz, S. P. V., et al, *Chem. Ber.* 106:2950–2955 (1973).

*Primary Examiner*—Alan Siegel
*Attorney, Agent, or Firm*—Connolly and Hutz

[57] ABSTRACT

Process for the preparation of hexafluoropropene dimers having a high proportion of perfluoro-(4-methyl-2-pentene)

The dimerization of hexafluoropropene produces almost exclusively dimers having a high content of perfluoro-(4-methyl-2-pentene) if the dimerization is carried out in an aprotic solvent in the presence of an adduct of an amine, which contains no NH groups, and a metal fluoride.

11 Claims, No Drawings

PROCESS FOR THE PREPARATION OF HEXAFLUOROPROPENE DIMERS HAVING A HIGH PROPORTION OF PERFLUORO-(4-METHYL-2-PENTENE)

DESCRIPTION

In the known dimerization of hexafluoropropene, the toxic perfluoro-(2-methyl-2-pentene) is formed, in some cases to a considerable extent, in addition to changing proportions of trimeric hexafluoropropene. It is known to separate the dimers from the trimers out of the crude distillation mixture and, for example, to isolate a mixture of 98% of trans-perfluoro-(4-methyl-2-pentene), in the following (I), in addition to 2% of perfluoro-(2-methyl-2-pentene), in the following (II), (U.S. Pat. No. 2,918,501, Example V). However, in this known process, about 4 times the amount of trimers is isolated in addition to the dimers.

The dimers of hexafluoropropene are suitable in many areas of use as a replacement for chlorofluorocarbons which are held responsible for the degradation of the ozone in the stratosphere. Considerable amounts of (II), on account of its toxicity, would obviously be unwanted in a substitute product. The object was therefore to prepare dimers of hexafluoropropene having as high as possible a proportion of (I) and as low as possible a proportion of (II), where as little as possible of the here unwanted trimers should be formed.

This object is achieved according to the invention by dimerizing hexafluoropropene in the presence of an adduct of an amine, which contains no N—H group, and a metal fluoride in an aprotic solvent.

Surprisingly, in this case, dimers are predominantly formed having a high content of (I) and little (II).

Halasz et al., Chem. Ber. 106 (1973) 2950 to 2955, disclosed first preparing, from triethanolamine and hexafluoropropene, tris-[2-(2H-hexafluoropropoxy)ethyl]amine and, using this in acetonitrile, catalyzing the oligomerization of hexafluoropropene. In this case, up to 90.5% of dimers are formed from which 96% of (I) and 3.9% of (II) could be isolated.

U.S. Pat. No. 4,042,638 discloses a process for the preparation of dimers and trimers of hexafluoropropene, in which hexafluoropropene is oligomerized by a crown ether in the presence of a complex salt of an alkali metal halide. Using a catalyst composed of potassium fluoride and 1,4,7,10,13,16-hexaoxacyclooctadecane, 87.2% of oligomers are obtained in this way containing 99.1% of dimers, where the dimer contained 95.8% of (I) and 4.2% of a mixture of the corresponding cis compound and (II).

All these known processes are complex and unsatisfactory with respect to the yield. In the process according to the invention, in contrast, the compound (I) is obtained simply and in a high yield and having a content of (II) which is so low that the crude product is usable directly.

The course of the process according to the invention must be regarded as surprising, since alkali metal fluorides as catalysts in the dimerization of hexafluoropropene can form (II) as the main product [Dresdner et al., J. Org. Chem. 30 (1965) 3524 to 3526]. Furthermore, it has been disclosed (Brunskill et al., Chem. Comm. 1970, 1444 to 1446), that the fluoride ion catalyzes the rearrangement of (I) into (II).

The abovementioned U.S. Pat. No. 2,918,501 discloses that hexafluoropropene can be reacted with halides, for example fluorides, and solvents selected from the group comprising the alkyl-substituted amides, phenylamines and sulfoxides, dimers and trimers being obtained. The highest yield of dimers in this case is obtained using dimethylaniline in methanol, but still more than 10% of trimers being obtained.

No indication is given by any of these known processes that the catalyst system used according to the invention forms the compound (I) highly selectively.

Preferred embodiments of the invention are described in more detail below.

The metal fluoride used is preferably potassium fluoride. The amine components used are preferably peralkylated, chelate-forming diamines or triamines, which can also contain ether oxygen in the alkyl groups or alkylene groups. The preferred ratio of amine nitrogen atoms to metal atom in the metal fluoride is 1:1 to 4:1. The complexes of amine and metal fluoride are prepared most simply by mixing the components in the solvent prior to the reaction with hexafluoropropene (HFP).

Preferred solvents are nitriles, for example acetonitrile, propionitrile or benzonitrile. Cyclic or open-chain ethers, for example tetrahydrofuran, 1,4-dioxane or diethylene glycol dimethyl ether give worse results.

All reagents should be as anhydrous as possible in order to avoid the formation of H-containing impurities.

The reaction of the catalyst solution with the HFP metered in in the gaseous state is carried out most simply in a stirred tank. The reaction temperature is preferably 35° to 60° C. After completion of the reaction, the reaction mixture separates into two phases. The crude HFP dimer separating out as the heavier phase is drained off. The catalyst solution remaining in the reactor can be used for the next batch.

The crude product is subjected to a water washing in order to free it from the residues of the catalyst and solvent. This purification operation is preferably carried out in counter-current. After separating off the washing water, the crude product is purified by distillation via a column having a well cooled receiver.

A typical preparation is described in Example 1. The tabulated Examples 2 to 9 were carried out using other catalyst systems.

The perfluoroisohexene obtained according to the invention is non-flammable, as is CFC 113 and thus has safety advantages versus the oils and glycols which are likewise used as CFC substitutes. Its ignition temperature at 420° C. is so high that it cannot become a hazard under the conventional use temperatures.

The perfluoroisohexene prepared according to the invention is a pure fluorocarbon compound, that is in contrast to CFC 113 it is chlorine-free and thus does not influence the ozone layer in the stratosphere. Its ozone degradation potential (ODP) is equal to zero. Because of its relatively reactive double bond, its life in the atmosphere is shorter than that of the saturated perfluoroalkanes which are likewise useful as CFC 113 substitutes. Because of its low acute mammalian (oral) toxicity, bacterial toxicity and fish toxicity, but poor biological degradability, the perfluoroisohexene obtained according to the invention is to be graded as only a slight hazard to water.

EXAMPLE 1

Preparation of hexafluoropropene dimers:

These experiments were carried out in a 16 l tank made of electropolished high-grade steel which is equipped with a controllable stirrer, a calibrated feed for gaseous hexafluoropropene and metered feeds for liquids and solids. Heating and cooling of the tank can be precisely controlled to ±1° C. via a circulation having an external plate heat exchanger.

A catalyst solution is first prepared in the laboratory from the following components:

1.5 l of acetonitrile (dehydrated via distillation over a little calcium hydride and storage over a 3 Å molecular sieve), 69.7 g (0.6 mol) of N,N,N',N'-tetramethylethylenediamine (dried over a 4 Å molecular sieve), 34.9 g (0.6 mol) of potassium fluoride powder (dried by stirring the powder at 180° C./0.5 mbar).

The components are added together under dry nitrogen in this sequence with the stirrer running and are intensively stirred at 30° to 40° C. for 1 hour. A yellowish solution is obtained which contains virtually no solid potassium fluoride.

This solution is charged into the 16 l tank which has been carefully flushed with nitrogen. The tank is heated to 40° C. with the head valve closed and 16 kg of gaseous HFP are then metered in in the course of 6 hours with the stirrer running. The reaction is slightly exothermic. The internal temperature is kept at 40° to 50° C. by cooling. The mixture is then allowed to continue to react for a further 2 hours at 40° C. and is then cooled to 15° C. with the stirrer shut off.

14 kg of crude product are slowly drained off via the bottom valve of the tank into a vessel which, for pressure compensation, is connected by the HFP feed-line to the tank (breathing pipe). 2 kg of the product remain with the lighter catalyst phase in the tank.

The crude product is analyzed by gas chromatography. A packed column (5% GEXE 60 on Porasil C) equipped with a thermal conductivity detector is used for the analysis (carrier gas: helium). The assignment of the components was established previously by determination of the retention times and area factors using substantially pure reference compounds. The following distribution of the fluorine-containing products is obtained:

| | |
|---|---|
| $CF_3—CF=CF_2$ | 0.2% |
| $(CF_3)_2CFH$ | 0.1% |
| trans-$(CF_3)_2CF—CF=CF—CF_3$ (I) | 90.1% |
| cis—$(CF_3)_2CF—CF=CF—CF_3$ | 5.0% |
| $(CF_3)_2C=CF—CF_2CF_3$ (II) | 0.4% |
| Σ HPP trimers | 4.2% |

By $^{19}F$-NMR analysis of the crude product (solution in $CDCl_3/R113$, Standard: $CF_3CO_2H$), it was confirmed that the ratio of trans- and cis-HFP dimers determined by GC corresponds to the molar ratio of these two compounds. This was determined by evaluating the integrals of the fluorine atoms bound at the double bond. The $^{19}F$-NMR characteristic data of the two isomers are listed below (Standard: trifluoroacetic acid).

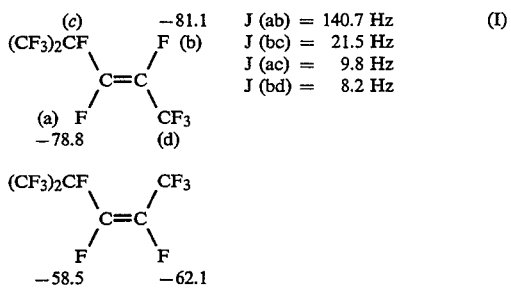

Two further batches were carried out using the catalyst solution remaining in the tank, where in each case 14 kg of HFP were reacted. After the third batch in total, the catalyst solution was separated off from the product.

The GC analysis gave the following product distributions:

| | Batch 2 | Batch 3 |
|---|---|---|
| $CF_3CF=CF_2$ | 0.5% | 1.0% |
| $(CF_3)_2CFH$ | 0.1% | 0.2% |
| trans-$(CF_3)_2CF—CF=CF—CF_3$ (I) | 90.1% | 90.3% |
| cis—$(CF_3)_2CF—CF=CF—CF_3$ | 5.1% | 5.0% |
| $(CF_3)_2C=CF—CF_2CF_3$ (II) | 0.4% | 0.2% |
| $(CF_3)_2CH—CF_2CF_3$ | 0.1% | 0.1% |
| Σ HFP trimers | 3.7% | 3.2% |

The highly toxic perfluoro-2-methyl-1-pentene could not be detected in any batch.

In total, by combination of the crude products, 43.5 kg were obtained. This material still contained traces of impurities which originate from the catalyst solution. It was purified by counter-current washing in a vertical bubble column packed with Raschig rings. The column was filled with 10 l of water. The fluoro product was metered in at the head and trickled over the column. At the same time, in counter-current, 20 l of water were introduced at the bottom end. The purified product collected at the bottom end of the column in a collection vessel. After separation off of a supernatant water layer, the product (43 kg) contained less than 0.005% of water.

For final purification, the washed product was distilled at atmospheric pressure over a packed column, the condenser and receiving vessel of which were cooled with the aid of a refrigeration unit to 0° C. The main fraction obtained was 40 kg having a boiling range from 45.5° to 49.5° C. Composition according to GC:

| | |
|---|---|
| $CF_3—CF=CF_2$ | 0.1% |
| trans-$(CF_3)_2CF—CF=CF—CF_3$ (I) | 94.1% |
| cis—$(CF_3)_2CF—CF=CF—CF_3$ | 4.9% |
| $(CF_3)_2C=CF—CF_2CF_3$ (II) | 0.2% |
| Σ HFP trimers | 0.7% |

The mass yield is 90% based on HFP used.

EXAMPLES 2 TO 9

The components of the catalyst system (metal fluoride and amine) were stirred with the solvent in a stirred flask under a protective gas (nitrogen or argon) for 1 hour at 30° to 40° C. This mixture was then placed under protective gas into a 300 ml stirred autoclave made of high-grade steel. With the stirrer running, 150 g (1.0 mol) of hexafluoropropene were injected in in gaseous state in the course of 30 minutes and the mixture was stirred for a further 1.5 hours. The crude product was separated off from the catalyst solution in a separating funnel and was shaken with a water/ice mixture in the separating funnel. The product phase thus obtained was weighed and analyzed by GC. The results are presented in the following table.

TABLE

| Example No. | Metal fluoride | | | Amine | | | Solvent | | Reaction temp. (°C.) | Product (g) | Composition (%) | | | | | |
|---|---|---|---|---|---|---|---|---|---|---|---|---|---|---|---|---|
| | Type | g | mol | Type | g | mol | Type | ml | | | 1 | 2 | 3 | 4 | 5 | 6 |
| 2 | KF | 1.49 | 0.025 | I | 6.72 | 0.055 | $CH_3CN$ | 60 | 40 | 127 | 0.2 | 0.2 | 80.8 | 4.0 | 0.6 | 14.2 |
| 3 | KF | 1.49 | 0.025 | II | 8.08 | 0.025 | $CH_3CN$ | 50 | 24 | 146.9 | 0.2 | 0.3 | 90.9 | 4.1 | 1.8 | 2.7 |
| 4 | KF | 1.49 | 0.025 | III | 5.05 | 0.025 | $CH_3CN$ | 50 | 40–60 | 145.6 | 1.0 | 0.3 | 89.5 | 5.3 | 0.3 | 3.6 |
| 5 | KF | 1.49 | 0.025 | IV | 4.35 | 0.025 | $CH_3CN$ | 50 | 30 | 143 | 0.3 | 0.2 | 83.8 | 3.9 | 5.7 | 6.1 |
| 6 | KF | 1.49 | 0.025 | V | 4.3 | 0.025 | $CH_3CN$ | 50 | 20–40 | 145.7 | 0.2 | 0.3 | 74.0 | 4.3 | 17.0 | 4.2 |
| 7 | $MnF_2$ | 1.16 | 0.0125 | VI | 2.9 | 0.025 | $CH_3CN$ | 50 | 20 | 145.9 | 0.4 | 0.2 | 89.6 | 4.4 | 1.7 | 3.7 |
| 8 | KF | 1.49 | 0.025 | VI | 2.9 | 0.025 | $C_3H_7CN$ | 50 | 40 | 139.8 | 0.2 | 0.2 | 88.0 | 4.0 | 2.5 | 5.0 |
| 9 | KF | 1.49 | 0.025 | VI | 5.8 | 0.5 | DEGDM | 50 | 60 | 125 | 0.1 | 0.1 | 66.4 | 5.2 | 16.0 | 12.2 |

I: $N(CH_3)_2C_6H_5$,
II: $N(CH_2CH_2OCH_2CH_2OCH_3)_3$,
III: $(CH_3)_2N(CH_2)_3—O—CH_2CH_2N(CH_2CH_3)_2$,
IV: $(CH_3)_2N(CH_2)_3—O—(CH_2)_2N(CH_3)_2$,
V: $CH_3N[CH_2CH_2N(CH_3)_2]_2$,
VI: $(CH_3)_2NCH_2CH_2N(CH_3)_2$.
DEGDM: $CH_3OCH_2CH_2OCH_2CH_2OCH_3$
1: $CF_3CF=CF_2$,
2: $(CF_3)_2CFH$,
3: trans-$(CF_3)_2CF—CF=CF—CF_3$,
4: cis-$(CF_3)_2CF—CF=CF—CF_3$,
5: $(CF_3)_2C=CF—CF_2CF_3$,
6: Σ HFP trimers

We claim:

1. A process for the preparation of dimers of hexafluoropropene having a high proportion of perfluoro-4-methyl-2-pentene) and a low content of perfluoro-(2-methyl-2-pentene), which comprises: dimerizing hexafluoropropene in acetonitrile, benzonitrile, or proprionitrile, in the presence of catalytic amounts of an adduct of a metal fluoride and an amine which does not contain NH groups and wherein each nitrogen of said amine is bound to three substituents, which substituents are each selected from the group consisting of alkyl, alkylene, alkyl containing ether oxygen, and alkylene containing ether oxygen.

2. The process as claimed in claim 1, wherein the said amine is a diamine or triamine.

3. The process as claimed in claim 1, wherein each alkyl or alkylene group has up to 4 carbon atoms.

4. The process as claimed in claim 1, wherein in the said adduct the ratio of amine nitrogen atoms to the metal atom of the metal fluoride is 1:1 to 4:1.

5. The process as claimed in claim 1, wherein the said metal fluoride is potassium fluoride.

6. The process as claimed in claim 4, wherein the said metal fluoride is potassium fluoride.

7. The process as claimed in claim 1, wherein the said adduct is prepared from the said amine and the said metal fluoride in situ in the said solvent.

8. A process for the preparation of dimers of hexafluoropropene having a high proportion of perfluoro-(4-methyl-2-pentene) a low content of perfluoro-(2-methyl-2-pentene), which comprises dimerizing hexafluoropropene in acetonitrile, benzonitrile, or proprionitrile in the presence of catalytic amounts of an adduct of a metal fluoride and an amine which, per nitrogen atom, has three alkyl or alkylene groups which optionally contain ether oxygen groups, and said amine does not contain NH groups, whereby a major proportion of the dimerization product thereby formed is trans-$(CF_3)_2CF—CF=CF—CF_3$.

9. A process that is claimed in claim 8, wherein the trans-$(CF_3)_2CF—CF=CF$ $CF_3$ dimerization product is formed in an amount of at least 66.4% of the total reaction products by weight.

10. A process that is claimed in claim 9, wherein the trans-$(CF_3)_2CF—CF=CF—CF_3$ dimerization product is formed in an amount of at least 74.0% of the total reaction products by weight.

11. A process that is claimed in claim 8, wherein the trans-$(CF_3)_2CF—CF=CF—CF_3$ dimerization product is formed in an amount of at least 80.8% of the total reaction products by weight.

* * * * *